United States Patent [19]

Holmwood et al.

[11] Patent Number: 4,744,817
[45] Date of Patent: May 17, 1988

[54] TRIAZOLE DERIVATIVES

[75] Inventors: Graham Holmwood, Wuppertal; Karl H. Büchel, Burscheid; Paul Reinecke, Leverkusen; Wilhelm Brandes, Leichlingen; Gerd Hänssler, Leverkusen, all of Fed. Rep. of Germany

[73] Assignee: Bayer Aktiengesellschaft, Leverkusen, Fed. Rep. of Germany

[21] Appl. No.: 835,824

[22] Filed: Mar. 3, 1986

[30] Foreign Application Priority Data

Mar. 22, 1985 [DE] Fed. Rep. of Germany ....... 3510411

[51] Int. Cl.$^4$ ................ C07D 249/08; A01N 43/653; A61K 31/41
[52] U.S. Cl. ...................... 71/92; 514/184; 514/383; 548/101; 548/262
[58] Field of Search ............... 548/262, 104, 341, 336; 71/92; 514/383, 184

[56] References Cited

U.S. PATENT DOCUMENTS 3,892,764 7/1975 Metzger et al. ............ 548/341
4,215,220 7/1980 Richter et al. ............. 548/341
4,436,548 3/1984 Zeeh et al. .

FOREIGN PATENT DOCUMENTS 0054974 6/1982 European Pat. Off. .......... 548/341
3202601 8/1983 Fed. Rep. of Germany ....... 548/262
2159148 11/1985 United Kingdom ............ 548/262

Primary Examiner—Richard L. Raymond
Assistant Examiner—D. L. Dinner
Attorney, Agent, or Firm—Sprung, Horn, Kramer & Woods

[57] ABSTRACT

Novel triazole of the formula

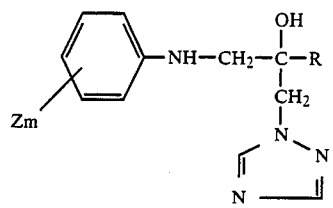

in which
R represents alkyl, cycloalkyl or the groupings

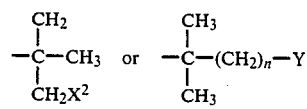

wherein
$X^1$ represents hydrogen or halogen,
$X^2$ represents halogen,
Y represents alkoxy, alkylthio, halogenoalkoxy, halogenoalkylthio, alkenyl, alkoxycarbonyl, cyano, optionally substituted phenoxy, optionally substituted phenyl, optionally substituted phenylthio, optionally substituted phenylalkoxy or optionally substituted phenylalkylthio and
n represents the number 0, 1 or 2,
Z represents halogen, alkyl, halogenoalkyl, halogenoalkoxy, halogenoalkylthio or phenyl and
m represents the number 0, 1, 2, or 3, or addition products thereof with acids and metal salts, which exhibit fungicidal and plant growth-regulating activity.

9 Claims, No Drawings

TRIAZOLE DERIVATIVES

The present invention relates to new triazole derivatives, several processes for their preparation, and their use as fungicides and plant growth regulators.

It has already been disclosed that a large number of 1-hydroxyalkyl-azolyl derivatives possess fungicidal and plant growth-regulating properties (see U.S. patent application Ser. No. 683,891, filed Dec. 20, 1984, now pending). Thus for example, 2-(4-chlorophenylthiomethyl)-3,3-dimethyl-1-(1,2,4-triazol-1-yl)-butan-2-ol can be used as a fungicide. However, the activity of this substance is not always satisfactory, especially when small amounts are used.

It has also been disclosed that zinc ethylene-1,2-bisdithiocarbamate is very suitable for combating fungal plant diseases (see Phytopathology 33, 1113 (1963)). However, the disadvantage of using this substance is that the effect is not always sufficient at low dosages.

New triazole derivatives of the formula

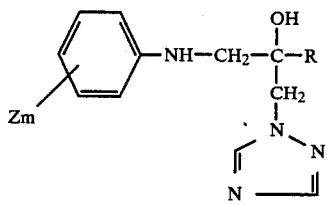
(I)

in which

R represents alkyl, cycloalkyl or the groupings

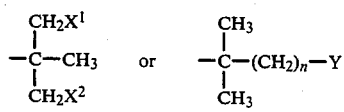

wherein $X^1$ represents hydrogen or halogen, $X^2$ represents halogen,

Y represents alkoxy, alkylthio, halogenoalkoxy, halogenoalkylthio, alkenyl, alkoxycarbonyl, cyano, optionally substituted phenyl, optionally substituted phenoxy, optionally substituted phenylthio, optionally substituted phenylalkoxy or optionally substituted phenylalkylthio and n represents the number 0, 1 or 2, Z represents halogen, alkyl, halogenoalkyl, halogenoalkoxy, halogenoalkylthio or phenyl and m represents the number 0, 1, 2 or 3, and their acid addition salts and metal salt complexes have now been found.

The compounds of the formula (I) possess an asymmetrically substituted carbon atom and can therefore occur in the form of the two optical isomers. The present invention relates both to the isomer mixtures and to the individual isomers.

It has furthermore been found that new triazole derivatives of the formula (I) and their acid addition salts and metal salt complexes are obtained if (a) oxiranes of the formula

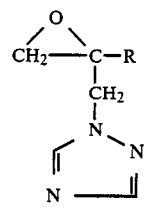
(II)

in which

R has the meaning given above, are reacted with aniline derivatives of the formula

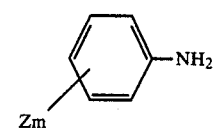
(III)

in which

Z and m have the meaning given above, in the presence of a diluent; or (b) acetanilides of the formula

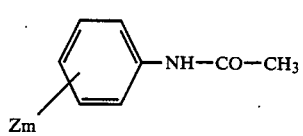
(IV)

in which

Z and m have the meaning given above, are treated with strong bases in the presence of a diluent, and the resulting products are then reacted with oxiranes of the formula

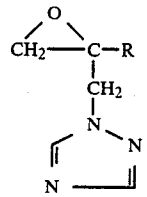
(II)

in which

R has the meaning given above, in the presence of a diluent; and, if appropriate, the resulting compounds of the formula (I) are then subjected to an addition reaction with an acid or a metal salt.

It has also been found that the substances according to the invention possess powerful fungicidal and plant growth-regulating properties.

Surprisingly, the active compounds according to the invention, of the formula (I), and their acid addition salts and metal salt complexes exhibit a substantially better fungicidal and plant growth-regulating action than 2-(4-chlorophenyl-thiomethyl)-3,3-dimethyl-1-(1,2,4-triazol-1-yl)-butan-2-ol, which is a known active compound having a similar constitution and suitable for the same indication. Moreover, the compounds according to the invention also possess a better fungicidal action than zinc ethylene-1,2-bisdithiocarbamate, which is known from the prior art and is a similar compound in terms of its action.

Formula (I) gives a general definition of the triazole derivatives according to the invention. In this formula, R preferably represents straight-chain or branched alkyl having 1 to 6 carbon atoms, cycloalkyl having 3 to 8 carbon atoms or the groupings of the formulae

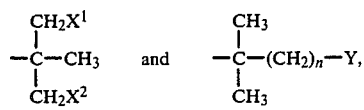

wherein $X^1$ preferably represents hydrogen, fluorine, chlorine or bromine, $X^2$ preferably represents fluorine, chlorine or bromine, Y preferably represents alkoxy having 1 to 6 carbon atoms, alkylthio having 1 to 6 carbon atoms, halogenoalkoxy having 1 or 2 carbon atoms and 1 to 5 identical or different halogen atoms, halogenoalkylthio having 1 to 2 carbon atoms and 1 to 5 identical or different halogen atoms, alkenyl having 2 to 6 carbon atoms, alkoxycarbonyl having 1 to 4 carbon atoms in the alkoxy part, cyano, phenyl, phenoxy, phenylalkoxy having 1 to 4 carbon atoms in the alkoxy part and phenylalkylthio having 1 to 4 carbon atoms in the alkylthio part, it being possible for each of these phenyl, phenoxy, phenylalkoxy and phenylalkylthio radicals to be monosubstituted or polysubstituted by identical or different substituents from amongst halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cyclohexyl, dialkylamino having 1 to 4 carbon atoms in each alkyl part, nitro, cyano and alkoxycarbonyl having 1 to 4 carbon atoms in the alkoxy part, and n represents the numbers 0, 1 or 2, Z preferably represents fluorine, chlorine, bromine, alkyl having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 to 2 carbon atoms and 1 to 5 identical or different halogen atoms, or phenyl, and m represents the numbers 0, 1, 2 or 3.

Particularly preferred compounds of the formula (I) are those in which

R represents straight-chain or branched alkyl having 1 to 4 carbon atoms, cycloalkyl having 3 to 6 carbon atoms or the groupings of the formulae

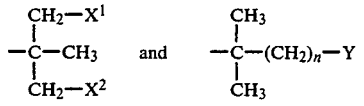

wherein $X^1$ represents hydrogen, fluorine, chlorine or bromine, $X^2$ represents fluorine, chlorine or bromine, Y represents methoxy, ethoxy, methylthio, ethylthio, trifluoromethyl, trifluoromethylthio, vinyl, methoxycarbonyl, ethoxycarbonyl, cyano and phenyl, phenoxy, phenylmethoxy and phenylmethylthio, it being possible for each of these phenyl, phenoxy, phenylmethoxy and phenylmethylthio radicals to be monosubstituted to trisubstituted in the phenyl part by identical or different substituents from amongst fluorine, chlorine, methyl, ethyl, methoxy, methylthio, trifluoromethyl, trifluoromethoxy, trifluoromethylthio, cyclohexyl, dimethylamino, methoxycarbonyl and/or ethoxycarbonyl, n represents the numbers 0, 1 or 2, Z represents fluorine, chlorine, bromine, methyl, ethyl, tert.-butyl, trifluoromethyl, trifluoromethoxy, trifluoromethylthio or phenyl and m represents the numbers 0, 1, 2 or 3.

Other preferred compounds according to the invention are addition products of acids and those triazole derivatives of the formula (I) in which the substituents R and Z and the index m have the meanings which have already been mentioned as being preferred.

The acids which can be used for the addition reactions preferably include hydrohalic acids, such as, for example, hydrochloric acid and hydrobromic acid, in particular hydrochloric acid, and phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example, p-toluenesulphonic acid and naphthalene-1,5-disulphonic acid.

Other preferred compounds according to the invention are addition products of salts of metals of main groups II to IV and of subgroups I and II and IV to VIII of the periodic table of elements and those triazole derivatives of the formula (I) in which the substituents R and Z and the index m have the meanings which have already been mentioned as being preferred.

In this connection, salts of copper, of zinc, of manganese, of magnesium, of tin, of iron and of nickel are particularly preferred. Suitable anions of these salts are those which are derived from acids which lead to physiologically acceptable addition products. In this connection, particularly preferred acids of this type are hydrohalic acids, such as, for example, hydrochloric acid and hydrobromic acid, and phosphoric acid, nitric acid and sulphuric acid.

If 2-tert.-butyl-2-(1,2,4-triazol-1-yl-methyl)-oxirane and 3,4-dichloroaniline are used as starting materials, the course of process (a) according to the invention can be represented by the following equation:

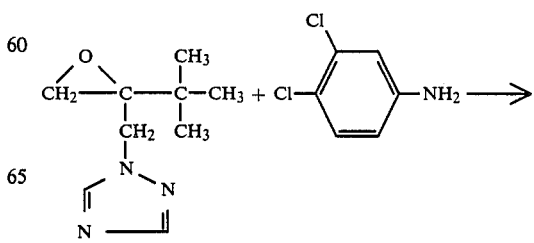

-continued

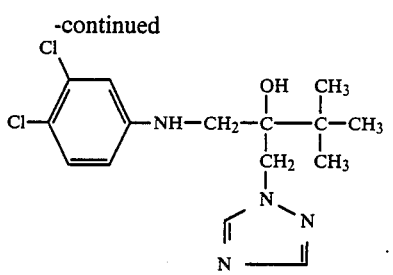

If 4-chloro-acetanilide is used as a starting material, sodium hydride as the base and 2-tert.-butyl-2-(1,2,4-triazol-1-yl-methyl)-oxirane as a reactant, the course of process (b) according to the invention can be represented by the following equation:

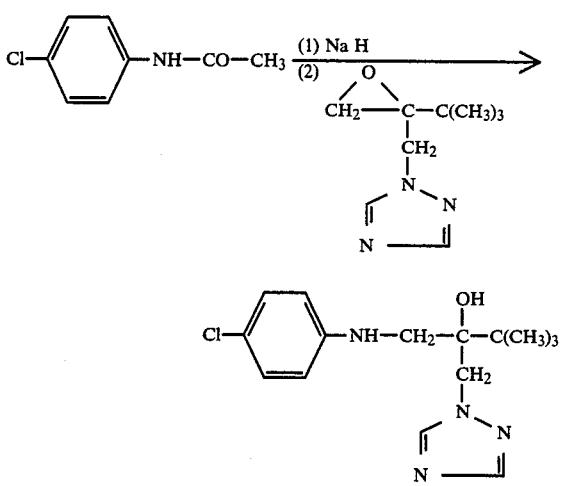

Formula (II) gives a definition of the oxiranes required as starting materials in carrying out process (a) according to the invention.

In this formula, R preferably has those meanings which have already been mentioned in connection with the description of the substances according to the invention, of the formula (I), as being preferred for this substituent.

The oxiranes of the formula (II) are already known or can be prepared in a simple manner by methods which are known in principle (see U.S. patent application Ser. No. 683,891).

Formula (III) gives a definition of the aniline derivatives furthermore required as starting materials in carrying out process (a) according to the invention. In this formula, Z and m preferably have those meanings which have already been mentioned in connection with the description of the substances according to the invention, of the formula (I), as being preferred for this substituent or this index.

The aniline derivatives of the formula (III) are generally known compounds.

Suitable diluents for the reaction of process (a) according to the invention are all polar inert solvents. Alcohols, such as methanol, ethanol and propanol, and strongly polar organic solvents, such as dimethylformamide and dimethyl sulphoxide, as well as water, are preferably used.

Mixtures of polar organic solvents and water, for example mixtures of alcohols, such as ethanol, and water, are particularly preferred.

In carrying out process (a) according to the invention, the reaction temperatures can be varied within a relatively wide range. In general, the reaction is carried out at temperatures between 20° and 180° C., preferably between 60° and 150° C.

Process (a) according to the invention is carried out in general under atmospheric pressure. However, it is also possible to employ elevated pressure of up to 10 bar of reduced pressure.

Process (a) according to the invention is carried out in general using 1 to 5 mols, preferably 1 to 3 mols, of the aniline derivative of the formula (III) per mol of the oxirane of the formula (II). Working-up is effected by customary methods. In general, the reaction mixture is evaporated down, water is added to the residue, the resulting mixture is extracted with an organic solvent, the organic phase is evaporated down and the residue which remains is purified chromatographically or by recrystallization.

Formula (IV) gives a definition of the acetanilides required as starting materials in process (b) according to the invention. In this formula Z, and m preferably have those meanings which have already been mentioned in connection with the description of the substances according to the invention, of the formula (I), as being preferred for this substituent or this index.

The acetanilides of the formula (IV) are generally known substances of organic chemistry.

Suitable strong bases for carrying out process (b) according to the invention are all customary strong inorganic and organic bases. Alkali metal hydrides, such as sodium hydride, and lithium compounds, such as butyl-lithium, as well as alkali metal alcoholates, such as sodium methylate, sodium ethylate and potassium tert.-butylate, are preferably used.

Suitable diluents for carrying out process (b) according to the invention are all customary inert organic solvents. Ethers, such as diethyl ether, tetrahydrofuran and dioxane, as well as strongly polar solvents, such as dimethylformamide and dimethyl sulphoxide, are preferably used.

In carrying out process (b) according to the invention, the reaction temperatures can be varied within a relatively wide range. In the treatment of the compounds of the formula (IV) with strong bases, temperatures between 0° and 50° C., preferably between 20° and 30° C., are generally employed. In the subsequent reaction with oxiranes of the formula (II), temperatures between 20° and 180° C., preferably between 60° and 150° C., are generally employed.

Process (b) according to the invention is carried out in general under atmospheric pressure. However, it is also possible to employ elevated or reduced pressure.

In carrying out process (b) according to the invention, acetanilides of the formula (IV) are generally reacted with an equivalent amount of a strong base and an equivalent amount of an oxirane of the formula (II) is then added. However, it is also possible to use an excess of either of the components. Working-up is effected by customary methods.

All acids which lead to physiologically acceptable salts are suitable for the preparation of acid addition salts of the compounds of the formula (I). Preferably used acids are those which have already been mentioned in connection with the description of the substances according to the invention as being acids which are preferably used for the addition reaction.

The acid addition salts of the compounds of the formula (I) can be prepared in a simple manner by customary salt formation methods. In general, a compound of the formula (I) is dissolved in a suitable inert diluent, and an acid is then added. Isolation is effected in a known manner, for example by filtering off the salt and, if appropriate, purifying it by washing with an inert organic solvent.

Preferred salts for the preparation of metal salt complexes of the compounds of the formula (I) are salts of those metals which have already been mentioned in connection with the description of the substances according to the invention as being metals which are preferably used for the addition reaction. Hydrohalic acids, such as, for example, hydrochloric acid and hydrobromic acid, and phosphoric acid, nitric acid and sulphuric acid are preferred as anions of these metal salts.

The metal salt complexes of compounds of the formula (I) can be prepared in a similar manner by customary methods. In general, a metal salt is dissolved in an alcohol, such as, for example, ethanol, and a compound of the formula (I) is then added. Isolation is likewise effected in a known manner, for example by filtering off the metal salt complex and, if appropriate, purifying it by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds and of the soil.

As plant protection agents, the active compounds according to the invention can be used with particularly good success for combating those fungi which cause powdery mildew diseases; thus, for combating Erysiphe species, such as, for example, against the powdery mildew of barley or of cereal causative organism (*Erysiphe graminis*). The active compounds according to the invention are also very suitable for combating the causative organisms of Pyricularia and Pelliculariaia rice and against rust (*Uromyces appendiculatus*) in beans.

The fact that the active compounds according to the invention not only display a protective action but also have a systemic action should be particularly singled out. Thus, it is possible to protect plants from fungal infestation if the active compound is fed to the above-ground parts of the plants via the soil and the roots or via the seed.

The active compounds according to the invention also possess plant growth-regulating properties.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talcs, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, nonionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the substances according to the invention are employed as fungicides, the amount used can be varied within a relatively wide range, depending on the method of application. Thus, in the treatment of parts of plants, the concentrations of active compounds in the use forms are in general between 1 and 0.0001% by weight, preferably between 0.5 and 0.001%. In the treatment of seed, amounts of active compound of from 0.001 to 50 g per kilogram of seed, preferably 0.01 to 10 g, are generally required. In the treatment of the soil, concentrations of active compound of from 0.00001 to 0.1% by weight, preferably from 0.0001 to 0.02%, are required at the place of action.

When the compounds according to the invention are employed as plant growth regulators, the amounts used can be varied within a relatively wide range. In general, 0.01 to 50 kg, preferably 0.05 to 10 kg, of active compound are used per hectare of soil area.

When the substances according to the invention are used as plant growth regulators, the rule is that they are applied within a preferred period of time, the exact definition of which depends on the climatic and vegetative circumstances.

The preparation and use of the active compounds according to the invention are illustrative by the examples which follow.

PREPARATION EXAMPLES

Example 1

(1)

[Structure: Cl,Cl-phenyl—NH—CH₂—C(OH)(C(CH₃)₃)—CH₂—(1,2,4-triazol-1-yl)]

A mixture of 16.2 g (0.1 mol) of 3,4-dichloroaniline and 18.1 g (0.1 mol) of 2-tert.-butyl-2-(1,2,4-triazol-1-yl-methyl)-oxirane in 150 ml of ethanol and 100 mol of water is boiled under reflux for 16 hours. Thereafter, the mixture is cooled to room temperature and evaporated down under reduced pressure by stripping off the solvent. Water is added to the residue which remains, and the resulting mixture is extracted with ethyl acetate. The combined organic phases are evaporated down under reduced pressure, and the residue which remains is purified chromatographically (silica gel column; mobile phase: 3:1 dichloromethane/ethyl acetate).

Evaporating down the eluate gives 6.7 g (19.5% of theory) of 1-(3,4-dichlorophenyl-amino)-3,3-dimethyl-2-(1,2,4-triazol-1-yl-methyl)-butan-2-ol, which has a melting point of 132°-133° C. after recrystallization from acetonitrile.

The substances listed in terms of their formulae in Table 1 below are also obtained by the method stated in Example 1 and in accordance with the stated process:

TABLE 1

(I)

[Structure: Zm-phenyl—NH—CH₂—C(OH)(R)—CH₂—(1,2,4-triazol-1-yl)]

| Example No. | $Z_m$ | R | Melting point (°C.) |
|---|---|---|---|
| 2 | 4-Cl | —C(CH₃)₃ | 87–89 |
| 3 | 2,4-Cl | —C(CH₃)₃ | 105–106 |
| 4 | 3-Cl | —C(CH₃)₃ | 110–112 |
| 5 | 2,4-CH₃ | —C(CH₃)₃ | 104–105 |

In the use examples which follow, the compounds stated below have been employed as comparative substances:

$$A = \begin{array}{c} CH_2-NH-CS-S \\ | \\ CH_2-NH-CS-S \end{array} \Big\rangle Zn$$

(disclosed in Phytopathology 33, 1113 (1963)).

$$B = [-Zn-S-\underset{\|}{C}-NH-CH_2-\underset{|}{CH}-NH-\underset{\|}{C}-S]_x$$
$$\phantom{B = [-Zn-S-C-NH-CH_2-}CH_3$$
(with S above each C, and CH₃ below CH)

(known)

Example A

Erysiphe test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds (2) and (4) according to the invention show better activity than the comparative substance (A).

Example B

Erysiphe test (barley)/curative

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are dusted with spores of Erysiphe graminis f.sp. hordei. 48 hours after the inoculation, the plants are sprayed with the preparation of active compound until dew-moist.

The plants are placed in a greenhouse at a temperature of about 20° C. and a relative atmospheric humidity of about 80%, in order to promote the development of powdery mildew pustules.

Evaluation is carried out 7 days after the inoculation.

In this test, the compounds (2) according to the invention shows better activity than the comparative substance (A).

Example C

Uromyces test (dwarf bean)/protective

Solvent: 4.7 parts by weight of acetone
Emulsifier: 0.3 parts by weight of alkylarlyl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (Uromyces appendiculatus) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, the compound (4) according to the invention shows better activity than the comparative substance (B).

Example D

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the compounds (2) and (4) according to the invention have a better action than the comparative substance (A).

Example E

Pyricularia Test (rice)/curative

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for curative activity, young rice plants are inoculated with an aqueous spore suspension of Pyricularia oryzae. The plants remain standing in a greenhouse at 25° C. and at a relative atmospheric humidity of 100% for 16 hours. After a short drying off period, the plants are sprayed with the wet preparation of active compound until dripping wet.

Evaluation of the disease infestation is carried out 4 days after the inoculation.

In this test, the compound (4) according to the invention shows better activity than the comparative substance (A).

Example F

Pyricularia test (rice)/systemic

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of Pyricularia oryzae. Thereafter, the plants remain in a greenhouse at a temperature of 25° C. and a relative atmospheric humudity of 100% until they are evaluated.

Evaluation of the disease infestation is carried out 4 days after the inoculation.

In this test, the compounds (2) and (4) according to the invention show better activity than the comparative substance (A).

Example G

Pellicularia test (rice)

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3- to 4-leaf stage are sprayed until dripping wet. The plants remain in a greenhouse until thay have dried off. The plants are then inoculated with Pellicularia sasakii and are placed at 25° C. and 100% relative atmospheric humidity.

The evaluation of the disease infestation is carried out 5 to 8 days after the inoculation.

In this test, the compounds (2) and (4) according to the invention show better activity than the comparative substance (A).

It will be understood that the specification and examples are illustrative but not limitative of the present invention and that other embodiments within the spirit and scope of the invention will suggest themselves to those skilled in the art.

We claim:

1. A triazole derivative of the formula

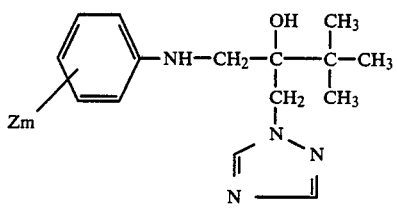

in which
X¹ represents hydrogen or halogen,
X² represents halogen,
Z represents fluorine, chlorine, bromine, alkyl, having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, or phenyl and
m represents the number 0, 1, 2 or 3, or an addition product thereof with an acid or metal salt.

2. A triazole derivative or addition product thereof according to claim 1, in which
X¹ represents hydrogen, fluorine, chlorine or bromine, and
X² represents fluorine, chlorine or bromine.

3. A compound according to claim 1, wherein such compound is 1-(3,4-dichlorophenyl-amino)-3,3-dimethyl-2-(1,2,4-triazol-1-yl-methyl)-butan-2-ol of the formula

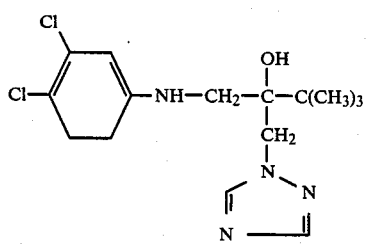

or an addition product thereof with an acid or metal salt.

4. A compound according to claim 1, wherein such compound is 1-(4-chlorophenyl-amino)-3,3-dimethyl-2-(1,2,4-triazol-1-yl-methyl)-butan-2-ol of the formula

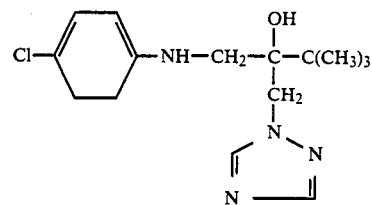

or an addition product thereof with an acid or metal salt.

5. A compound according to claim 1, wherein such compound is 1-(2,4-dichlorophenyl-amino)-3,3-dimethyl-2-(1,2,4-triazol-1-yl-methyl)-butan-2-ol of the formula

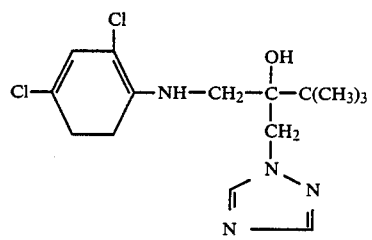

or an addition product thereof with an acid or metal salt.

6. A compound according to claim 1, wherein such compound is 1-(3-chlorophenyl-amino)-3,3-dimethyl-2-(1,2,4-triazol-1-yl-methyl)-butan-2-ol of the formula

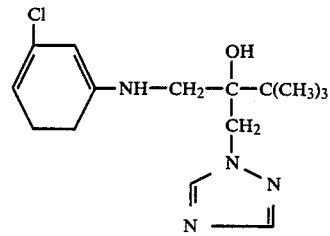

or an addition product thereof with an acid or metal salt.

7. A compound according to claim 1, wherein such compound is 3,3-dimethyl-1-(2,4-dimethylphenyl-amino)-2-(1,2,4-triazol-1-yl-methyl)-butan-2-ol of the formula

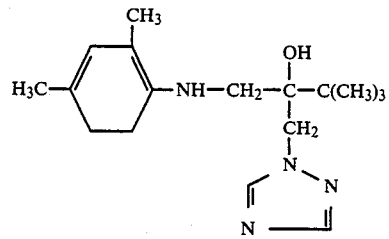

or an addition product thereof with an acid or metal salt.

8. A fungicidal or plant growth regulating composition comprising a fungicidally or plant growth regulating effective amount of a compound or addition product according to claim 1 in admixture with a diluent.

9. A method of combating fungi which comprises applying to such fungi or to a locus from which it is desired to exclude such fungi a fungicidally effective amount of a compound or addition product according to claim 1.

* * * * *